United States Patent
Fritz et al.

(10) Patent No.: US 7,130,046 B2
(45) Date of Patent: Oct. 31, 2006

(54) DATA FRAME SELECTION FOR CYTOMETER ANALYSIS

(75) Inventors: Bernard S. Fritz, Eagan, MN (US); Aravind Padmanabhan, Plymouth, MN (US); Peter Reutiman, Crystal, MN (US)

(73) Assignee: Honeywell International Inc., Morristown, NJ (US)

(*) Notice: Subject to any disclaimer, the term of this patent is extended or adjusted under 35 U.S.C. 154(b) by 42 days.

(21) Appl. No.: 10/950,898

(22) Filed: Sep. 27, 2004

(65) Prior Publication Data

US 2006/0066852 A1 Mar. 30, 2006

(51) Int. Cl.
*G01N 21/00* (2006.01)

(52) U.S. Cl. .................. 356/337; 356/336; 356/341

(58) Field of Classification Search ........ 356/335–343, 356/36–41; 422/82.05, 82.09, 82.11; 436/43, 436/63, 172–175; 250/573–575, 461.2
See application file for complete search history.

(56) References Cited

U.S. PATENT DOCUMENTS

| | | | |
|---|---|---|---|
| 3,822,095 A | 7/1974 | Hirschfeld | |
| 3,976,862 A | 8/1976 | Curbelo | |
| 4,281,924 A * | 8/1981 | Auer et al. .................. 356/73 |
| 4,478,076 A | 10/1984 | Bohrer | |
| 4,478,077 A | 10/1984 | Boher | |
| 4,501,144 A | 2/1985 | Higashi et al. | |
| 4,651,564 A | 3/1987 | Johnson et al. | |
| 4,683,159 A | 7/1987 | Bohrer et al. | |
| 4,695,034 A | 9/1987 | Shimizu et al. | |
| 4,745,279 A | 5/1988 | Karkar et al. | |
| 4,874,949 A | 10/1989 | Harris et al. | |
| 4,911,616 A | 3/1990 | Laumann, Jr. | |
| 4,953,978 A * | 9/1990 | Bott et al. .................. 356/336 |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,125,737 A * | 6/1992 | Rodriguez et al. ............ 356/39 |
| 5,129,794 A | 7/1992 | Beatty | |
| 5,171,132 A | 12/1992 | Miyazaki et al. | |
| 5,176,358 A | 1/1993 | Bonne et al. | |
| 5,185,641 A | 2/1993 | Igushi et al. | |

(Continued)

FOREIGN PATENT DOCUMENTS

EP 1001326 5/1999

(Continued)

OTHER PUBLICATIONS http://www.micronics.net/tsensor.htm, pp. 1-4, downloaded Jun. 14, 2000.

(Continued)

*Primary Examiner*—Gregory J. Toatley, Jr.
*Assistant Examiner*—Sang H. Nguyen
(74) *Attorney, Agent, or Firm*—Kris T. Fredrick

(57) ABSTRACT

A system for detecting when a core stream in a channel of a flow device is adequate for sufficient data accession. The system may determine the time period from the beginning of a sample run in a channel of a flow device to when the core stream is adequate. Data of detected FALS versus SALS light scattered by particles of the core stream may be plotted in data frames during a series of time intervals. The quality of the grouping and count rate of the data may indicate which frame and corresponding time interval reveal an adequate core stream.

42 Claims, 10 Drawing Sheets

U.S. PATENT DOCUMENTS

| | | | |
|---|---|---|---|
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,323,999 A | 6/1994 | Bonne et al. | |
| 5,441,597 A | 8/1995 | Bonne et al. | |
| 5,452,878 A | 9/1995 | Gravesen et al. | |
| 5,528,045 A | 6/1996 | Hoffman et al. | |
| 5,540,494 A * | 7/1996 | Purvis et al. | 356/73 |
| 5,570,193 A | 10/1996 | Landa et al. | |
| 5,601,080 A | 2/1997 | Oppenheimer | |
| 5,616,501 A | 4/1997 | Rodriguez et al. | |
| 5,633,724 A | 5/1997 | King et al. | |
| 5,683,159 A | 11/1997 | Johnson | |
| 5,684,575 A | 11/1997 | Steen | |
| 5,716,852 A | 2/1998 | Yager et al. | |
| 5,726,751 A | 3/1998 | Altendorf et al. | |
| 5,757,476 A | 5/1998 | Nakamoto et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,837,547 A | 11/1998 | Schwartz | |
| 5,863,502 A | 1/1999 | Southgate et al. | |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,939,326 A * | 8/1999 | Chupp et al. | 436/43 |
| 5,948,684 A | 9/1999 | Weigl et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,067,157 A * | 5/2000 | Altendorf | 356/337 |
| 6,082,185 A | 7/2000 | Saaski | |
| 6,084,670 A * | 7/2000 | Yamazaki et al. | 356/343 |
| 6,097,485 A | 8/2000 | Lievan | |
| 6,106,245 A | 8/2000 | Cabuz | |
| 6,109,889 A | 8/2000 | Zengerie et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,281,975 B1 | 8/2001 | Munk | |
| 6,382,228 B1 | 5/2002 | Cabuz et al. | |
| 6,549,275 B1 | 4/2003 | Cabuz et al. | |
| 6,750,060 B1 * | 6/2004 | Ozasa et al. | 436/10 |
| 6,784,981 B1 * | 8/2004 | Roche et al. | 356/39 |

FOREIGN PATENT DOCUMENTS

| | | | |
|---|---|---|---|
| JP | 08271509 A * | 10/1996 | |
| WO | WO95/27199 | 3/1995 | |
| WO | WO99/60397 | 4/1999 | |
| WO | WO01/09598 | 7/2000 | |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.

Altendorf et al., "Differential Blood Cell Counts Obtained Using A Microchannel Based Flow Cytometer", Solid State Sensors & Actuators, vol. 1, 531, 1997.

Altendorf et al., "Microfabrication Technology For Research And Diagnostics, Silicon Microchannel Optical Flow Cytometry", SPIE Proceedings, Biomedical Optics 96, Jan. 1996.

Altendorf et al., "Results Obtained Using A Prototype Microfluidics-Based Hematology Analyzer", SPIE Biomedical Optics 97, 1997.

Cubuz, et al., "Mesoscopic Sampler Based on 3D Array of Electrostatically Activated Diaphragms", Transducers '99, The 10th International Conference on Solid-State Sensors and Actuators, Digest of Technical Papers, vol. 2, Jun. 7-10, 1999.

Darling et al., "Integration Of Microelectrodes With Etched Microchannels For In-Stream Electrochemical Analysis", MicroTAS 98, Banff, Canada, Apr. 1998.

Hatch et al., "Microfluidic Approaches To Immunoassays", SPIE conference on Micromachining and Microfabrication Symposium at Santa Clara, CA, Sep. 20-22, 1999.

Huang. et al., "Development Of A Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10, No. 4, pp. 482-491, Dec. 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen, et al., "Four-Parameter White Blood Cell Differential Counting Based on Light Scattering Measurements", Alan R. Liss, Inc., Cytometery 9:39-43, 1988.

Weigl et al., "Silicon-microfabricated diffusion-based optical chemical sensor," Sensors and Actuators, B 38-39, pp. 452-457, 1997.

Weigl et al., "Diffusion-Based Optical Chemical Detection In Silicon Flow Structures", Analytical Methods & Instrumentation, μTTAS 96 special edition, 1996.

Weigl et al., "Microfluidic Diffusion-Based Separation And Detection", Science, vol. 283, pp. 346-347, Jan. 15, 1999.

Weigl et al., "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al., "Rapid Sequential Chemical Analysis Using Multiple Fluorescent Reporter Beads", μTTAS 96 Conference Proceedings, 1996.

Weigl et al., "Simultaneous Self-Referencing Analyte Determination In Complex Sample Solutions Using Microfabricated Flow Structures (T-Sensors™)", Proceedings of MicroTAS 98, 87-4, Banff, Canada, 1998.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorsSTm Technology", Medical Design Online, http://news.medicaldesignonline.com/featuresarticles/19990416-5922.html, Apr. 1999.

Weigl, et al., "Fluorescence and Absorbance Analyte Sensing In Whole Blood Based On Diffusion Separation In Silicon-Microfabricated Flow Structures," SPIE Proceedings, J. Lakowitz (ed.), Advances in Fluorescence Sensing Technology III, 1997, pp. 171-181.

Yager et al., "Design Of Microfluidic Sample Preconditioning Systems For Detection Of Biological Agents In Environment Samples", SPIE Proceedings, 3515, 252-259, 1998.

Yager et al., "Applying Microfluidic Chemical Analytical Systems To Imperfect Samples", Micro Total Analysis Systems 98, Kluwer Academic Publishers, Dordrecht, 207-212, 1998.

* cited by examiner

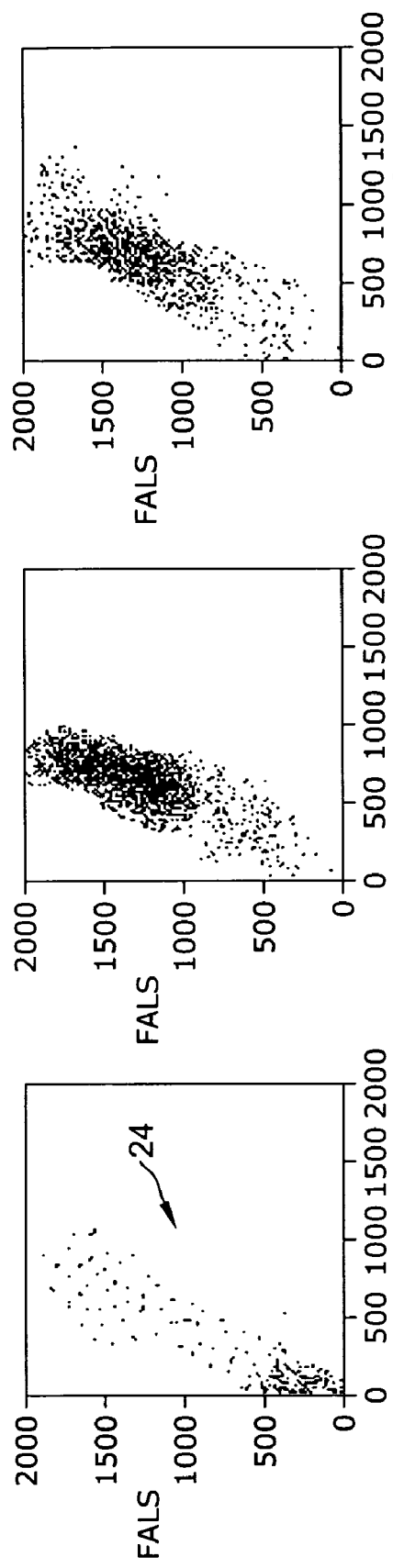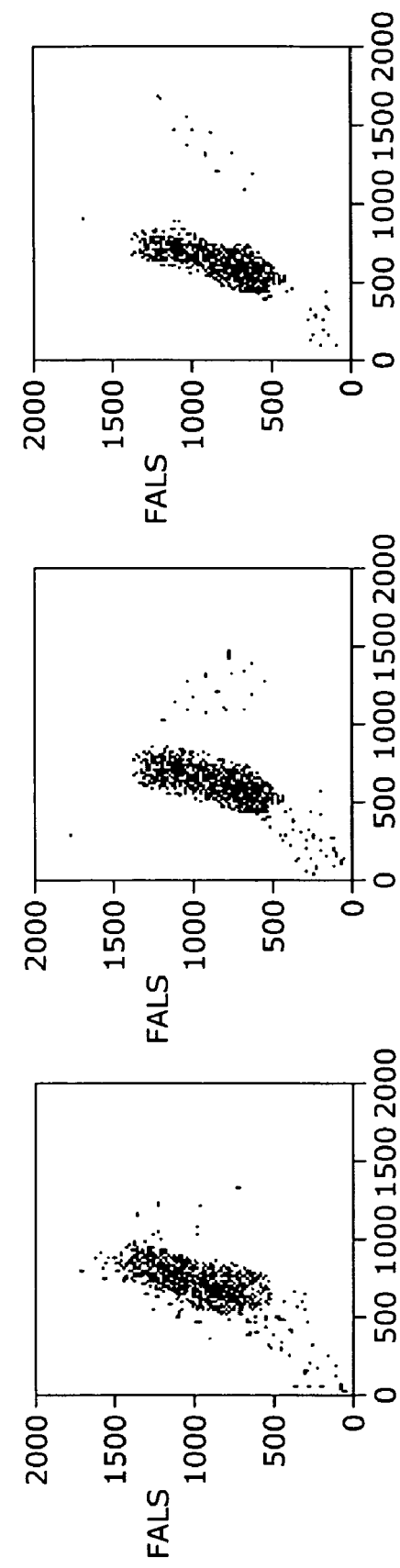

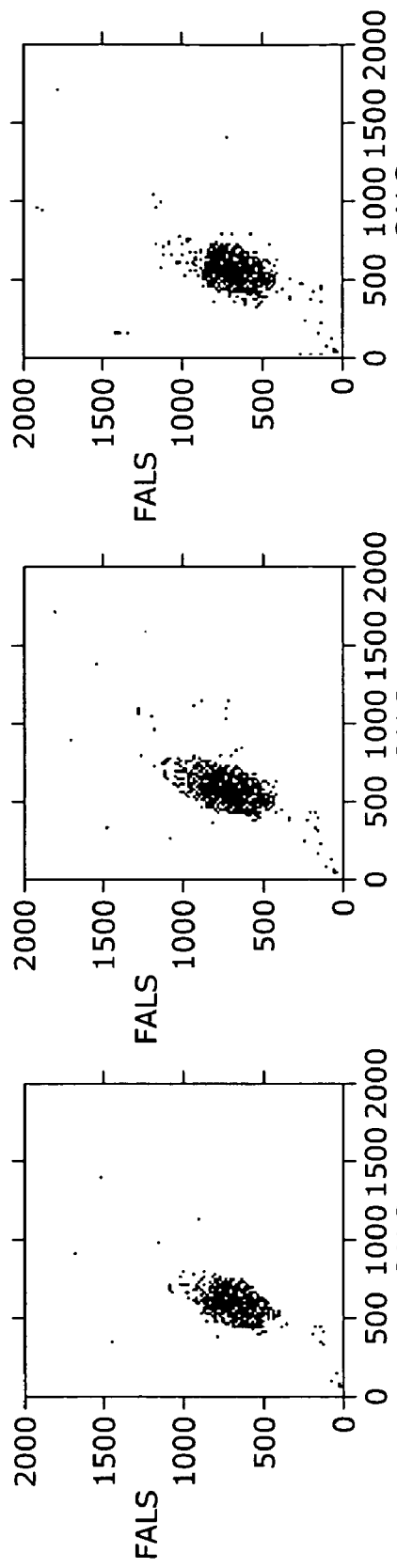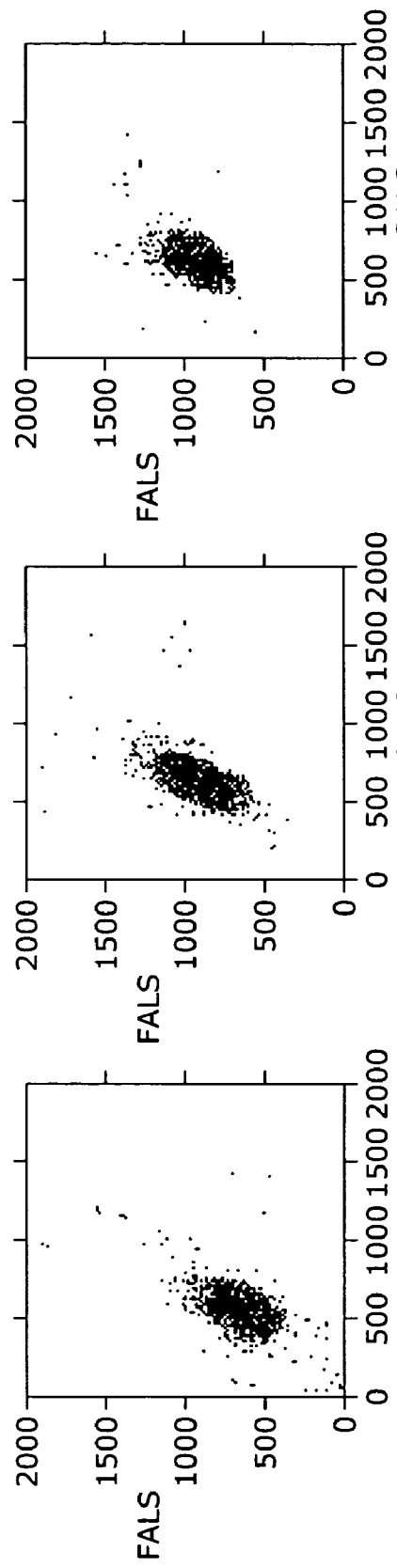

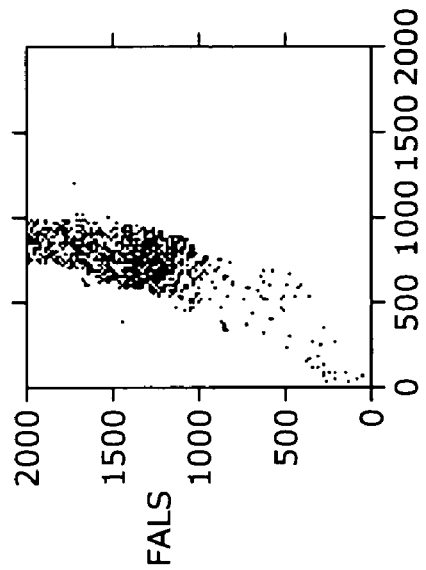
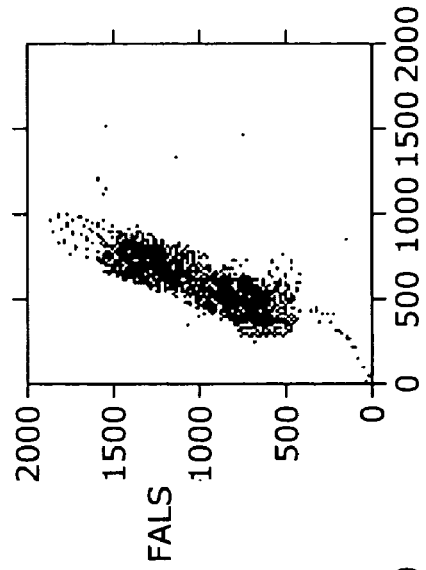
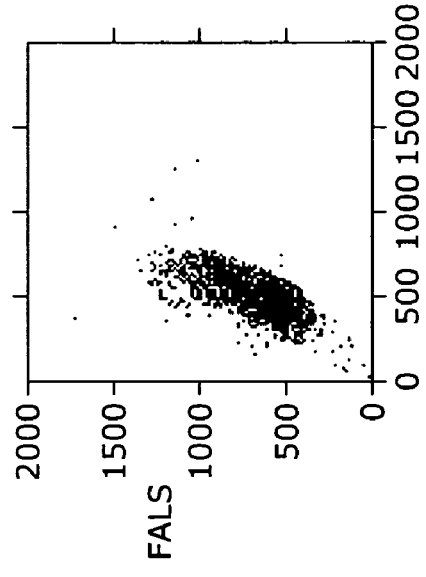
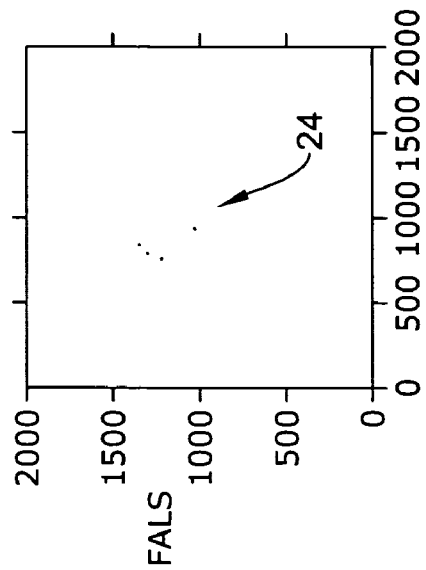
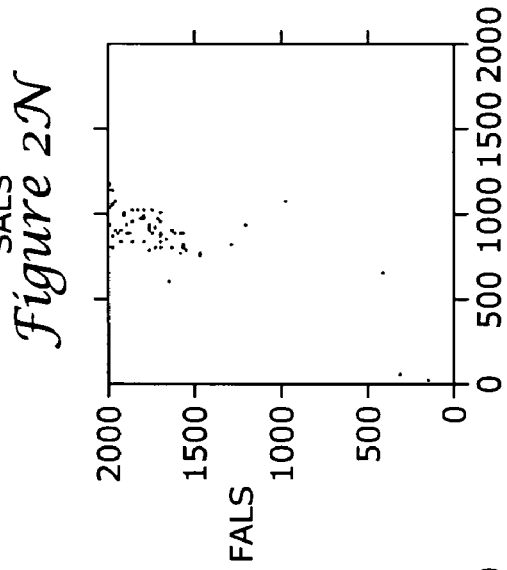
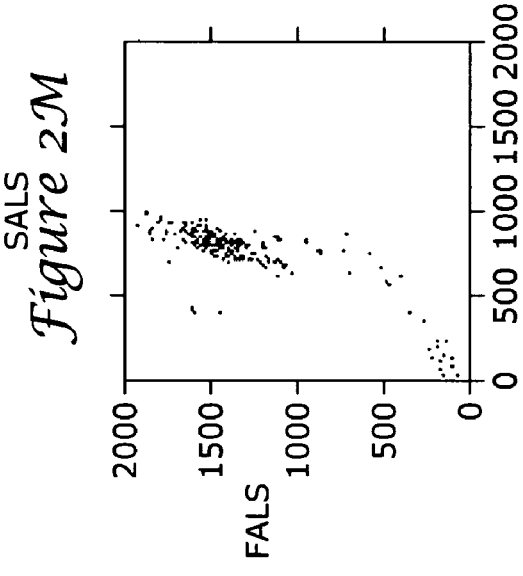
Figure 2M  Figure 2N  Figure 2O
Figure 2P  Figure 2Q  Figure 2R

DATA FRAME SELECTION FOR CYTOMETER ANALYSIS

BACKGROUND

The present invention relates to flow devices. Particularly, the invention relates to a characterization of a flow in a microfluidic device as used in flow devices. More particularly, the invention relates to selection of a data frame of a core stream of particles for adequate data accession.

SUMMARY

The present invention is a system for determining a time range where one or more characteristics of a core stream traveling through a flow channel of a microfluidic cartridge is optimum for data accession by a cytometer or other flow device. The system may provide a core stream through the flow channel for a period of time, the core stream having numerous particles that may be used to determine one or more flow characteristics. There may be an input light beam directed toward the core stream, where input light beam impinges some of the particles in the core stream. There may be a detecting of light scattered by the core stream. The detected output light may have information for monitoring one or more characteristics of the core stream. For instance, the number of particles moving per second in a flow channel by a detection mechanism may be one of the characteristics indicating an optimal or stable flow of a core stream of the particles in the core stream. These characteristics may indicate the appropriate time for reasonably accurate data taking from the core stream.

BRIEF DESCRIPTION OF THE DRAWING

FIGS. 2a–2s are illustrative diagrams of a core stream over a period of time with one-sized particles;

DESCRIPTION

A flow cytometer may use light scattering and fluorescence signatures to count and measure the properties of the particles as they move through a flow channel past an optical detection system. The cytometer may operate an optical detection system for a period of time before adequate measurements of the properties of the particles in the flow may be made. Particles in a flow may constitute a core stream. For a certain period of time after a start of a flow in a channel of a cytometer, the flow in the channel of the cytometer may become stabilized sufficiently for collecting adequately accurate data. Over an initial period of time, however, the flow does not necessarily have uniform characteristics. Due to the limited amount of a sample, the stability of the flow may be less in the beginning and at the end of the sample run being looked at. However, there may be a window of time when the flow of the core stream is stable for data taking. A figure of merit for a stable flow of a core stream may be indicated by the number of particles per second passing a detection mechanism in the flow channel. To achieve desirably accurate measurements about the core stream, a time from the start of a sample flow may be determined for a sufficiently stable core stream to occur. In seeking acceptable measurements of a core stream, multiple measurements may often be taken unnecessarily at numerous times when a sufficiently stable core stream does not exist, thereby wasting many test resources, such as blood, reagents, and electrical power. Minimizing measurements may reduce memory storage requirements, improve data acquisition time, shorten data processing loads, and decrease computer requirements.

The production or fabrication of microfluidic devices may result in the devices having a variation of flow characteristics among individual device structures. In other words, each cytometer or other flow type of device may have a different time lapse after the start of a sample run before achieving a stable flow for obtaining good measurements. Thus, one may have a system and/or approach for determining an optimum range of time during which to take measurements for each of various flow devices.

Figure 1:
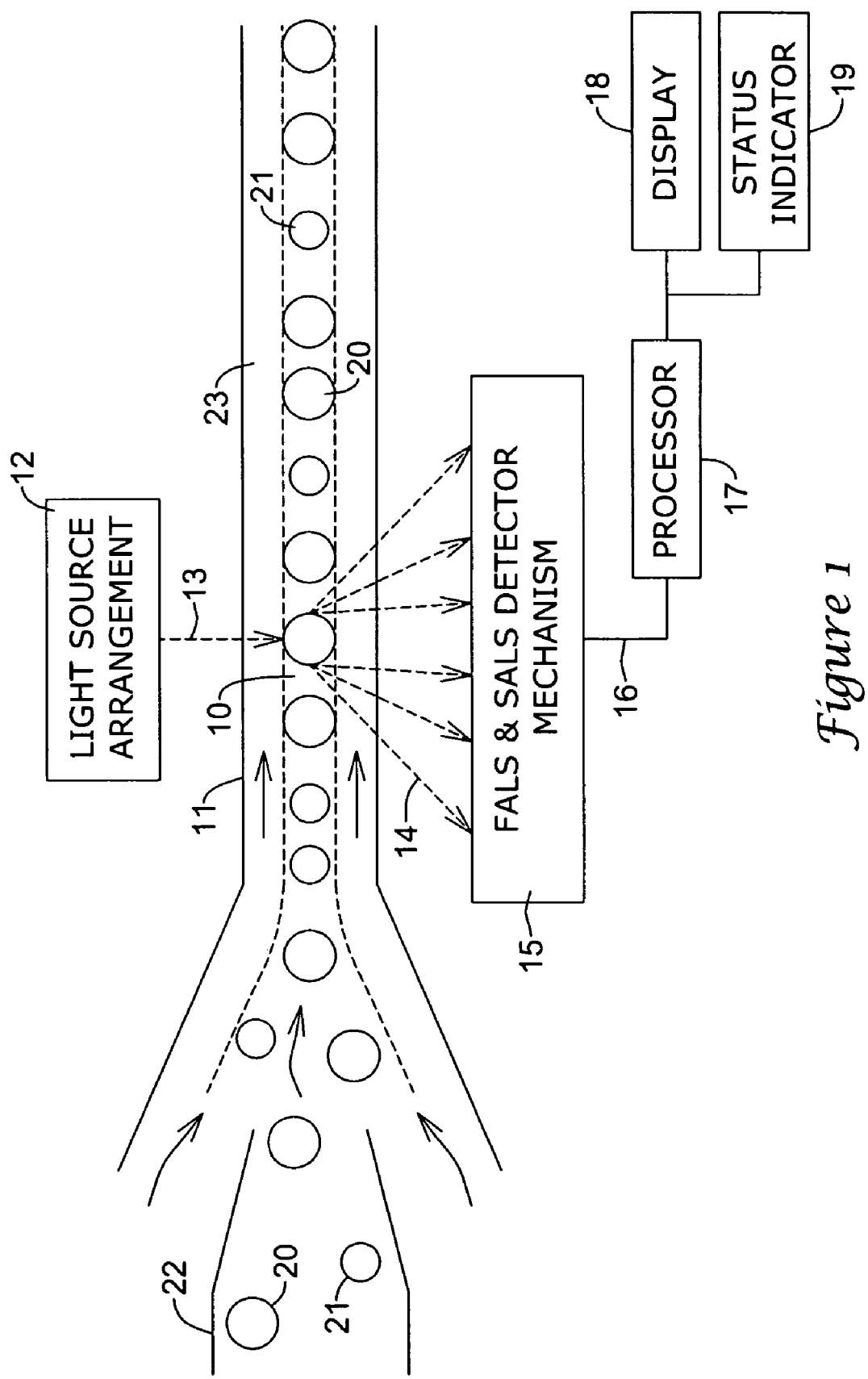
FIG. 1 is a schematic diagram of an illustrative flow channel and associated optical mechanism.

FIG. 1 is a schematic diagram of an illustrative flow channel and optical system used in flow cytometers. The figure is not necessarily drawn to scale. An illustrative example may include a light source 12, an input light beam 13, output light 14, a flow channel 11, a core stream 10, a detector mechanism 15, and an output 16. A number of particles 20 and 21 may be provided by a nozzle 22. As they enter the flow channel 11, a sheath fluid 23 may provide a laminar flow around the particles 20 and 21 to guide them into a single file as they flow through the channel 11.

In setting up a portable cytometer, for example, one may do runs using an approach to record output data as a function of time. A review of the data, such as a particle counts per unit of time of particles passing the detection mechanism or counter and data groupings in SALS versus FALS scattergrams, may determine which time frame reveals the most optimum core stream for data accession. The selected frame may then be the cytometer's window for recording data.

Figure 2S:
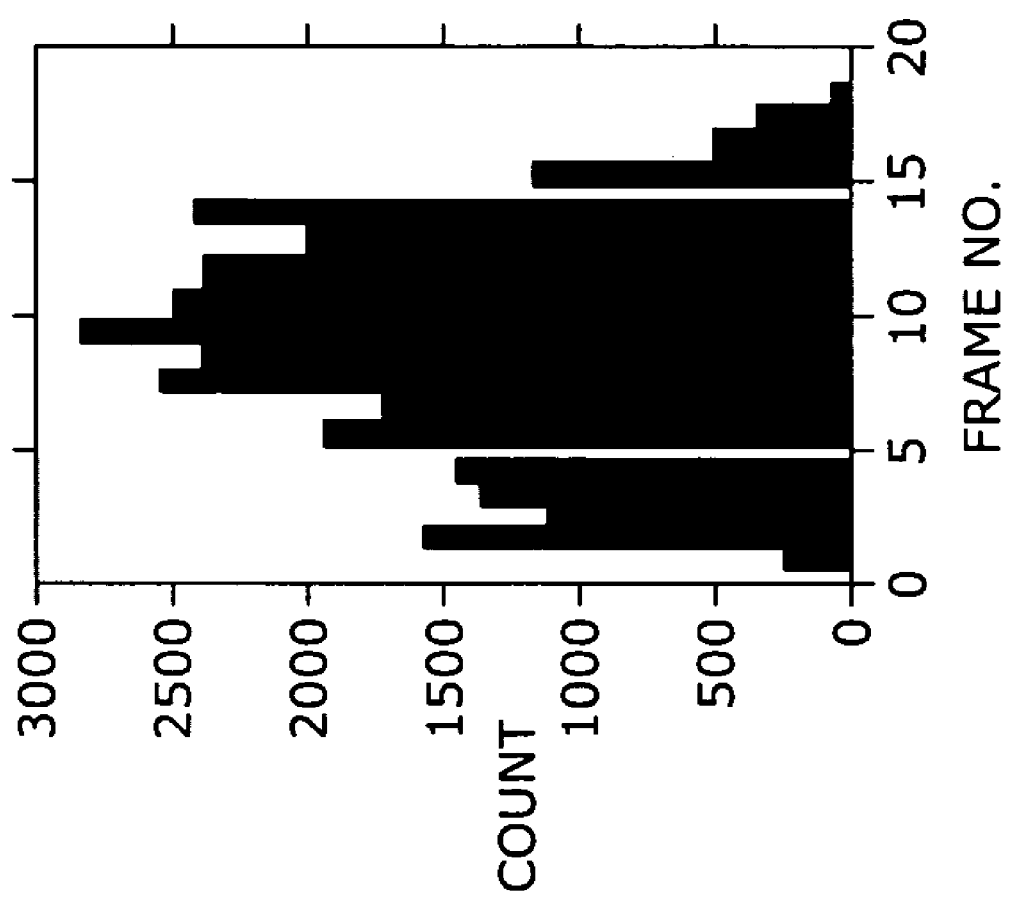
Figure 3A:
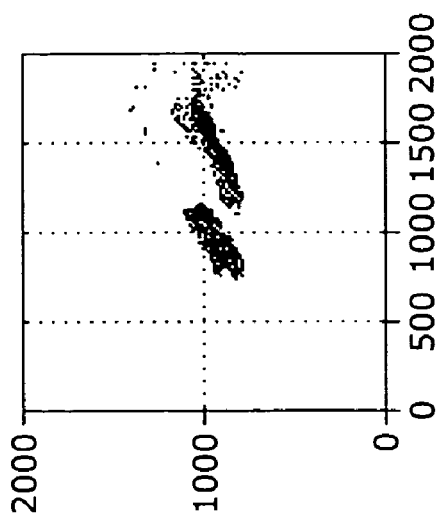
FIGS. 3a–3x are illustrative diagrams of a core stream over a period of time with two-sized particles.
Figure 3B:
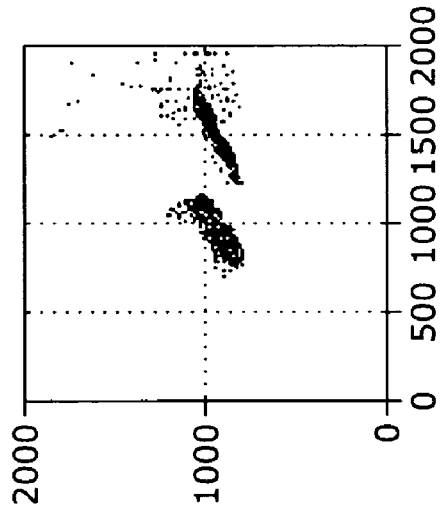
Figure 3C:
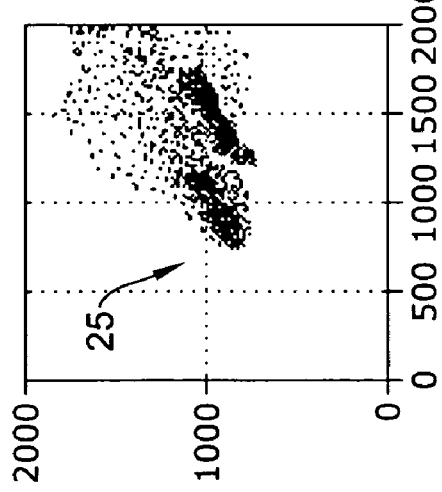
Figure 3D:
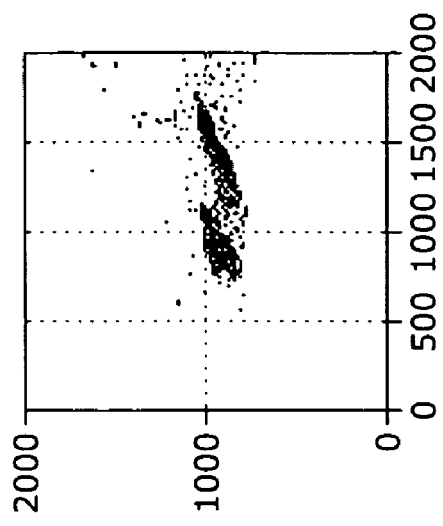
Figure 3E:
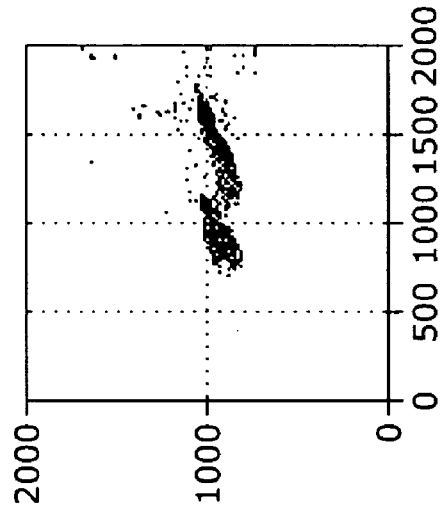
Figure 3F:
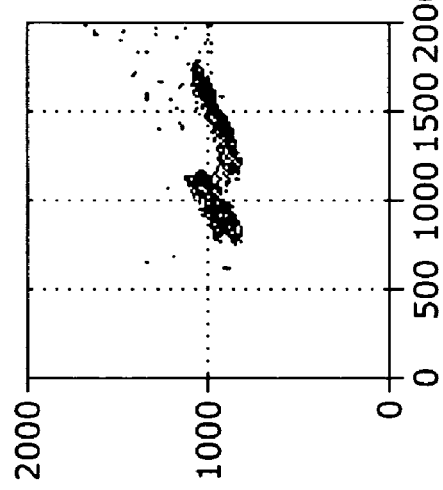
Figure 3G:
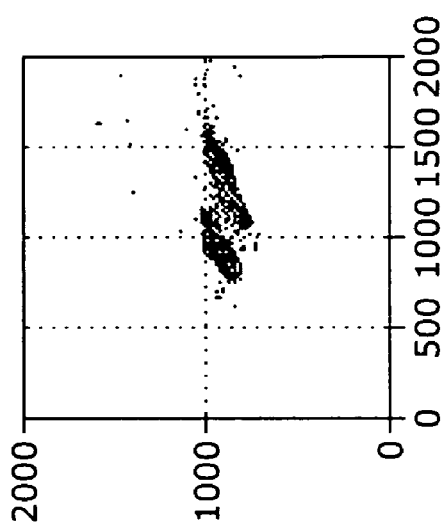
Figure 3H:
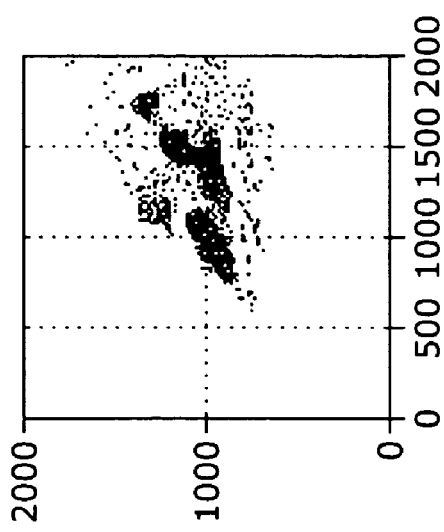
Figure 3I:
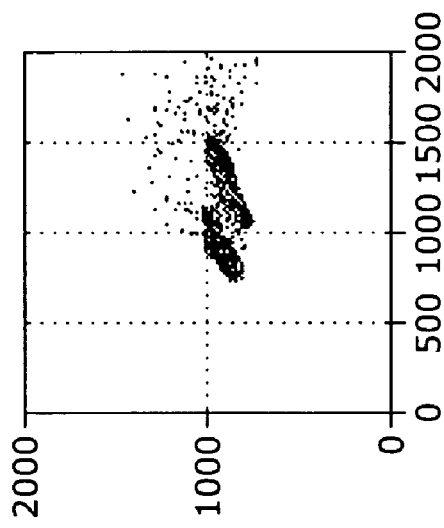
Figure 3J:
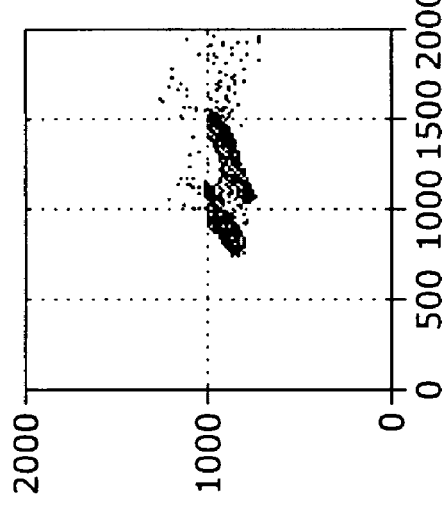
Figure 3K:
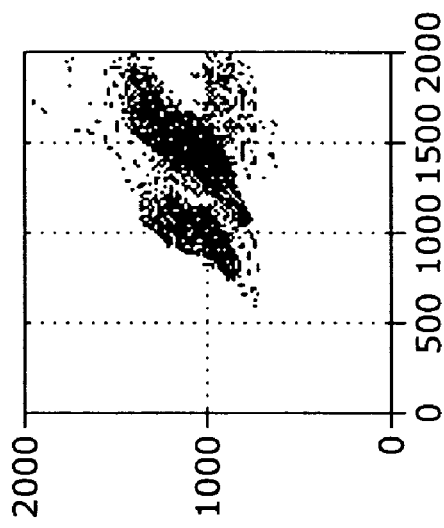
Figure 3L:
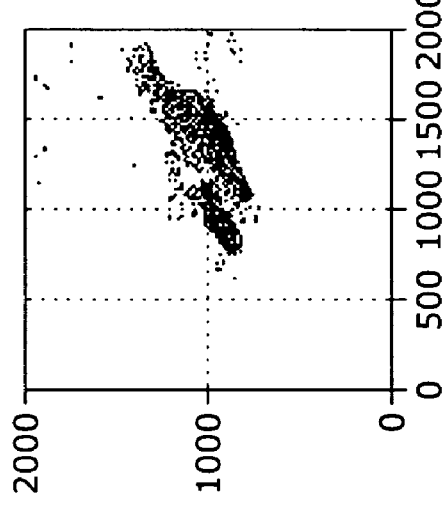
Figure 3M:
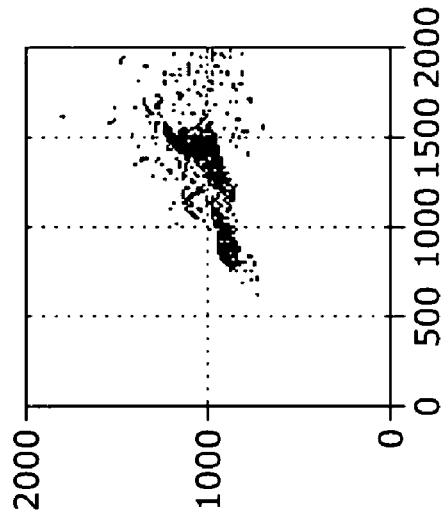
Figure 3N:
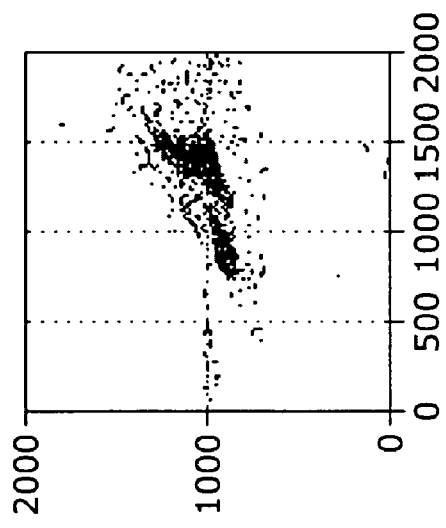
Figure 3O:
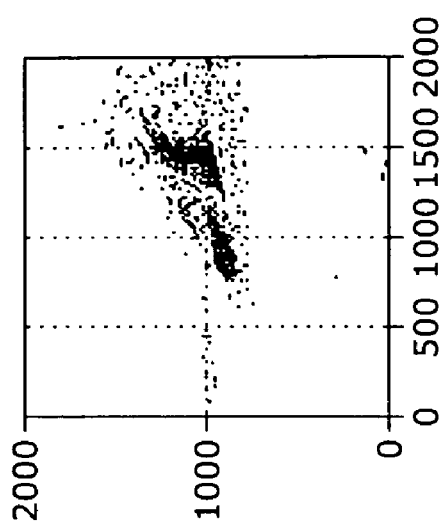
Figure 3P:
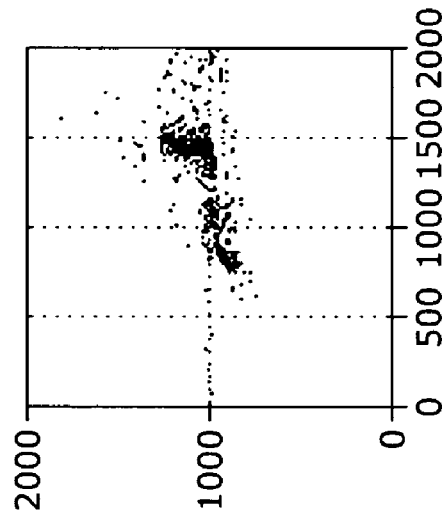
Figure 3Q:
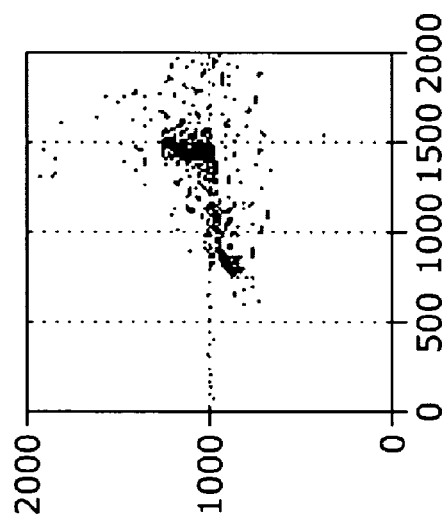
Figure 3R:
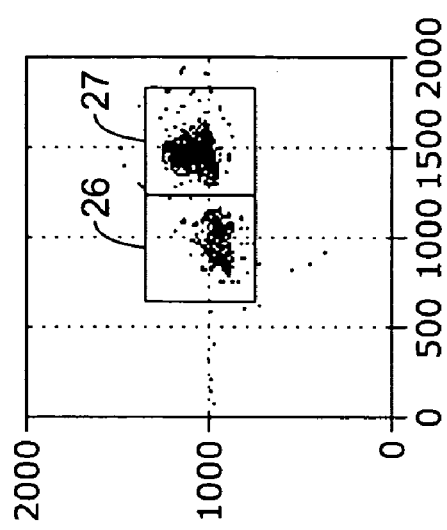
Figure 3S:
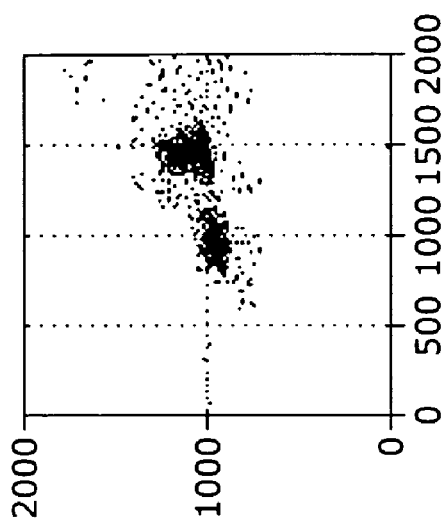
Figure 3T:
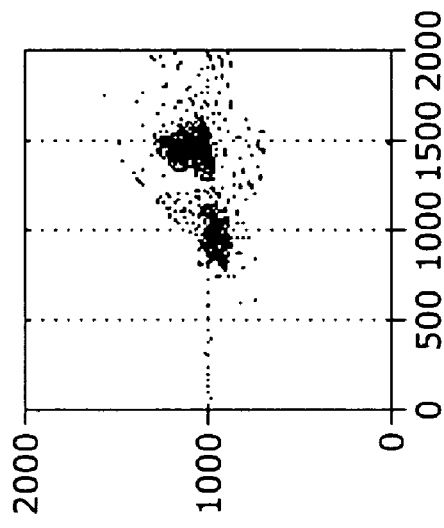
Figure 3U:
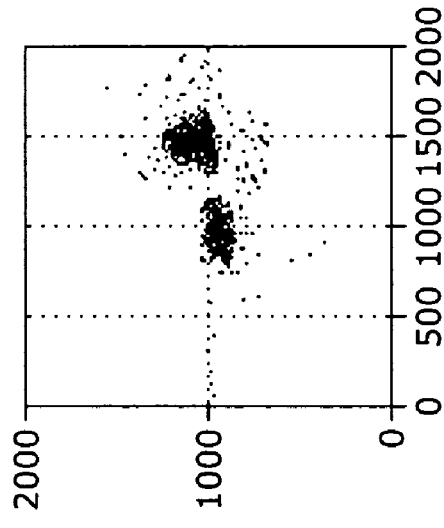
Figure 3V:
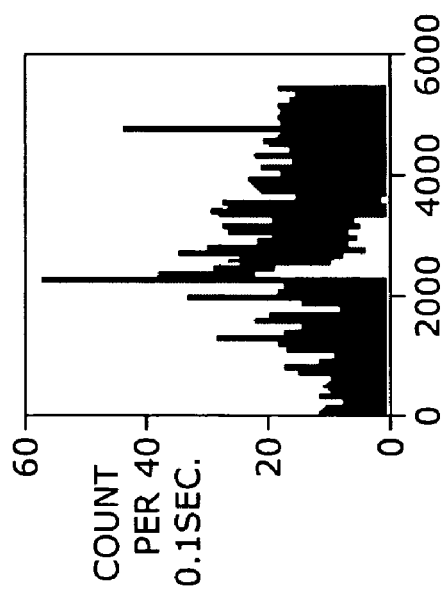
Figure 3W:
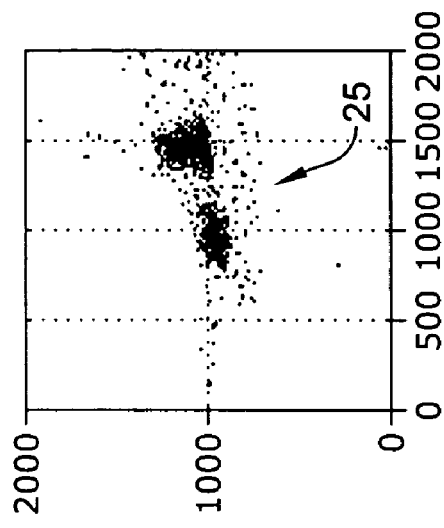

FIGS. 2a–2r show a measurement run done with 6 micron beads and FIGS. 3a–3w show a similar run done with 5 micron and 6 micron beads. In FIGS. 2a–2r is a series of scattergrams recorded over time as a bead flow began, stabilized and came to a finish. As the core of the stream 10 develops, a nicely packed group may be formed at some time that represents a sweetspot of the run.

The invention may determine the range of times after the start of the flow when one or more flow characteristics of the core stream 10 in a microfluidic cartridge are optimum for data collection. A group of particles may be inserted into a stream 10 formed by a laminar flow of a sheath fluid 23, which moves through the flow channel 11 for a period of time. The period of a run may be for about ninety seconds, but it may be any other period of time that is sufficient and appropriate. The test core stream 10 may contain artificial particles such as beads 20 and 21 to determine characteristics of the stream from the time of particle insertion through the end of the particle run. The input light beam 13 may be directed toward the core stream 10 from the light source arrangement 12. The light source arrangement 12 may contain one or more lasers, vertical cavity surface emitting lasers (VSCELs), edge emitting lasers, light emitting diodes (LEDs), or other sources of light. A portion of the input light beam 13 may be scattered as it passes through the flow channel 11 by particles 20 and 21 of the core stream 10. In actual data collection, the input light beam 13 may also excite fluorescence markers on particles from a sample for detection by fluorescent light detectors (not shown) to obtain specific information about particular particles in the core stream. But fluorescent light emissions are not necessary here for determining the time the core stream 10 has attained appropriate formation for data taking.

After the input light beam 13 passes through core stream 10 of the present system, the output light 14 may be detected by a FALS and SALS detector mechanism 15. Detector 15 may contain a linear array of detectors, an annular detector having several elements, or another detection mechanism. Detector mechanism 15 may provide signals at output 16 which may be recorded in scattergrams or frames of data collection over the time of a test sample run of a cytometer or flow device. This information may be used to determine the time range of various flow characteristics. One characteristic of interest in the core stream 10 may be its stability or alignment of particles in the stream. The core stream 10 may be less stable at the beginning and end of a sample run, or during another operational period of time, but be stable for some range of time between the start and the finish of the run. A sought after characteristic of the core stream 10 may be regarded as a stable flow adequate for data accession which is revealed by a tight grouping or a high quality of grouping of data in the scattergrams of the particles. Also, the rate of particles per unit of time moving through the flow channel may be regarded as another characteristic indicating the level of stability of the core stream 10. Other sought after characteristics of the core stream 10 may involve a less stable flow. Such other characteristics may include peculiar aspects of the core stream 10, which may be indicated by size, velocity, type, shape, structure, granularity, surface, antigens, and the like, about the particles in the core stream 10.

As the input light 13 enters the channel 11, it may impinge particles 20 and 21, and be scattered as light 14. Scattered light 14 may be detected at a forward angle light scattering (FALS) angle and a small angle light scattering (SALS) angle. The FALS angle may be 1–4 degrees and the SALS angle may be 4–13 degrees, as examples. These angles may be different for various detector designs. This scattering may be used to identify or determine certain characteristics of the core stream 10. If the FALS and SALS angles of the scattered light are known, as for instance from the detector mechanism 15, then certain information about particles 20 and 21 may be sought. Particles 20 and 21 may be beads having approximately the same size, even though FIG. 1 shows particles of two different sizes. For an illustrative example of testing for a good core stream 10, particles 20 and 21 may be regarded as beads having a 6 micron diameter. In other test runs, particles 21 may be regarded as beads having a 5 micron diameter but with particles 20 remaining as beads having a 6 micron diameter. The diameters of the beads or particles may have other sizes ranging from one to ten microns for certain applications.

In actual data accession, the particles 20 and 21 may be white blood cells. The white blood cells may be of five different types, including neutrophils, eosinophils, basophils, lymphocytes, and monocytes. By the angle of the light scattering, some types of the impinged white blood cells may be determined. A plot of FALS versus SALS data of the detected scattered light may be sufficient to identify some types of the white blood cells. However, objects or particles 20 and 21 may be other items of interest such as red blood cells in the core stream 10 in the flow channel 11. Applications in general may include particles relating to biological warfare and environmental matter as well as hematology.

FIGS. 2a through 2r show a series of frames 1–18, respectively, illustrating results of scattered light detected over a period of time of a core stream 10 having 6 micron beads such as particles 20 and 21. As the flow or cytometer system is operated for a period of time, a resulting output 16 from the detector 15 may go to a processor 17 and a display 18 to provide a sequentially ordered series of scattergrams or frames of data as FALS versus SALS plots, at constant intervals of time showing characteristics of the core stream 10. FIGS. 2a–2r show an overall period of time that may be ninety seconds with the output 16 providing a scattergram or frame of data at each five second interval, in each Figure. The data may be accumulated for five seconds into a frame and then a snapshot of the frame may be electronically taken, stored and/or displayed. Then, the displayed frame may be dumped and a new five second accumulation of data may occur for the next frame that is taken, stored and/or displayed. The time of each data accumulation interval and the total amount of time for attaining frames of core stream data may vary and be selected according to the type of flow sensor, circumstances and objectives of the testing at hand.

FIG. 2a shows the first frame of the run of the test. Same sized particles 20 and 21 may be represented by a plot of the FALS and SALS data for each particle of the core stream as it goes by the light source arrangement 12 and detector mechanism 15 over an interval of time. A dot 24 represents such data for each particle 20 or 21 that has scattered the light. For this run, the particles may be the 6 micron beads. The particles appear to be just beginning to enter flow channel 11 according the plotted dots 24 in FIG. 2a. This is evidenced by an ungrouped set of dots 24 and consequently reveals an unstable, unorganized or barely existent core stream 10 for that time frame.

The second scattergram or frame in FIG. 2b shows a significantly larger number of dots 24. FIG. 2s is a graph showing the number of dots 24 or detected particles per frame for frames 1–18 of FIGS. 2a–2r, where a trend of the population of the particles may be observed. Also, the counts or number of the particles for each frame is indicated in the respective Figure. Frames 3–8, respectively of FIGS. 2c–2h, show a progressive grouping of dots 24 which implies a formation of the core stream 10 with particles 20 and 21. Frame 9 of FIG. 2i appears to show the best formation or grouping of dots 24 implying the formation and stability of the core stream to be at an optimum level for data accession. Also, the number of particles of frame 9 appears to be favorable and may be a figure of merit for indicating the condition of the core stream relative to its optimum level of formation and stability for sufficient data accession. A standard deviation may be noted. A high or low count is not necessarily an indicator of an optimum condition of the core stream. A certain count may be a factor in addition to a certain grouping in determining an optimal core steam. What the certain count is may be affected by the composition of the core stream.

The time of the best appearing group appears to be at about 45 seconds after the start of the process or insertion of the particles. This duration may be the sought for characteristic of the particular flow device being tested. This may the most favorable time for taking data from a core stream of particles for the respective cytometer or flow device being tested.

Frames 10–17, respectively of FIGS. 2j–2q, appear to reveal a dispersion of the group of dots 24 and a corresponding indication of the decreasing grouping, form and stability of the core stream 10. These frames appear to indicate that the prime portion of the sample for being tested has already gone through the flow channel 11. Frame 18 of FIG. 2r shows the count of particles 20 to be close to zero, i.e., the end of the run of the sample of particles. The duration of time from the insertion of the particle sample to the best formation of the core stream 10 for data taking may vary from one flow device to another due to structural characteristics, fluid dynamics and possibly other device parameters.

If the core stream 10 is not very stable, output 16 may provide an unfocused, large group of dots 24 as shown in a display 18, as in frame 2 of FIG. 2b. If the core stream 10 is rather stable, the output 16 may provide a relatively smaller group of focused dots 24 as shown in frame 9 of FIG. 2i. The output 16 data may be analyzed to determine the time when the core stream 10 is sufficiently stable for an efficient and effective flow system operation. The output 16 may be analyzed via a processor 17 and a display 18 with visual observation, algorithms, computer computations, or any other workable approach or mechanism.

After analysis of the output 16 data of the core stream 10, a determination a desired range of time for optimum measurements or taking data may be made relative to operating the flow cytometer or other flow device. The data from output 16 may be processed directly into a status indication when the core stream is deemed having a status of unstable, borderline stable, or satisfactorily stable, which may be revealed in a status indicator 19, according to an algorithm and settings in the processor 17. Status information may be sent to a controller of the cytometer or other flow device to indicate that data taking may proceed after a certain duration of time after the start of the sample run. By determining the range of time for attaining the best data, sufficiently correct data may be obtained without the wasting of additional resources such as blood, reagents, time, electrical power, and the like, in flow cytometers or any other fluidic system.

The counts of particles for the frames 1–18 of the FIGS. 2a–2r, respectively may be 315, 1549, 1122, 1369, 1479, 1976, 1713, 2495, 2302, 2799, 2471, 2331, 1999, 2378, 1178, 468, 278 and 29. FIG. 2s is a graph of the particle counts per frame.

FIGS. 3a–3w are frames of scattergrams of an illustrative output 16 of a core stream 10 with particles 20 and 21. FIGS. 3a–3w are similar to FIGS. 2a–2r except that the core stream 10 in FIG. 3 contains two sizes of particles 20 and 21. Each scattergram may be a 10 second time frame of data that is accumulated for ten seconds, recorded and then dumped for the next accumulation of data for the next frame. FIG. 3a shows the first frame of the run of the test. Here, particles 20 and 21 having diameters 6 and 5 microns, respectively, may be represented by a plot of the FALS and SALS data as dots 25. For each particle of the core stream 10 there may be a FALS versus SALS dot 25 plotted in a scattergram as the particle goes by the light source arrangement 12 and detector mechanism 15. The particles of a sample in the core stream 10 may be a mixture of 6 and 5 micron beads. According the scattergram of FIG. 3a, there appears to be a somewhat ungrouped set of dots 25 implying an unstable or unorganized core stream 10 of particles 20 and 21 for that time frame.

The second scattergram or frame in FIG. 3b shows a significantly greater grouping of the large number of dots 25. Frames 3–8, respectively of FIGS. 3c–3h, show a progressive grouping of dots 25 which implies a better formation of the core stream 10 with particles 20 and 21. Frames 9–17, respectively of FIGS. 3i–3q, appear to reveal a slight to greater dispersion of the groups of dots 25 and a corresponding indication of the decreasing form and stability of the core stream 10 relative to groups 26 and 27, and then seem to improve up to frame 18 after frame 11 and an impending end of the sample run. Frame 18 of FIG. 3r appears to show the best formation or grouping of dots 25 into two groups 26 and 27 and an appropriate count implying the formation and stability of the core stream to be at an optimum level. This time frame of the seemingly best grouping of particles 20 and 21 appears to be one where data would be taken from the core stream 10, especially data that would be used for discriminating various properties of the various kinds of particles, such as size. These groups 26 and 27 may represent particles of 6 and 5 micron sizes, respectively. This may the most favorable time for taking data from a core stream of particles for the respective cytometer or flow device. Frames 19–23 of FIGS. 3s–3w tend to show a dispersion of the groups.

FIGS. 3a–3w appear to represent frames of scattergram data during a middle portion of the sample run and appear not to show data for the beginning and ending portions of the run. The frames or scattergrams shown by these Figures seem to indicate that the prime portion of the sample being tested or the most stable core stream 10 passes through the flow channel 11, for that run of the sample of particles. The optimal time of the run is when the groups of dots appear tightly packed and focused. The number of particles per unit time may also be an indicator of the optimal time of the run. The number of time intervals may be counted from the time of the start (not shown in this series of Figures) of the run multiplied by the time of each interval to get the optimum time for taking data from the core stream 10. There may be any number of other sized particles 20 and 21 in the core stream 10 that may resulting in other groupings of dots in the FALS versus SALS scattergrams.

Figure 3X:
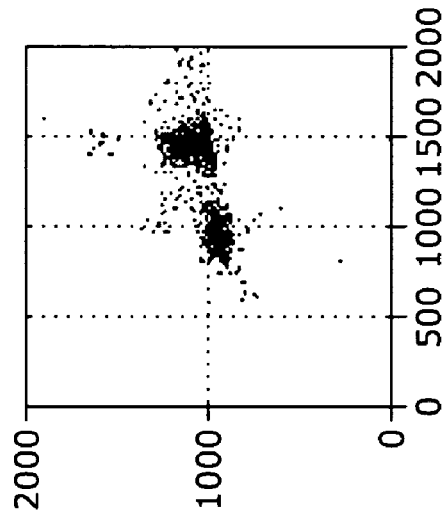

The count of particles per 0.1 second is shown in the graph of FIG. 3x. Very high or very low counts of particles do not necessarily indicate a frame of significant merit. The counts for frames 1–23 of FIGS. 3a–3w, respectively, may be 933, 753, 753, 703, 596, 776, 909, 841, 935, 2479, 6017, 3200, 2918, 2027, 1891, 1814, 2195, 1933, 1829, 1766, 1830, 1912 and 1796.

Figure 4:
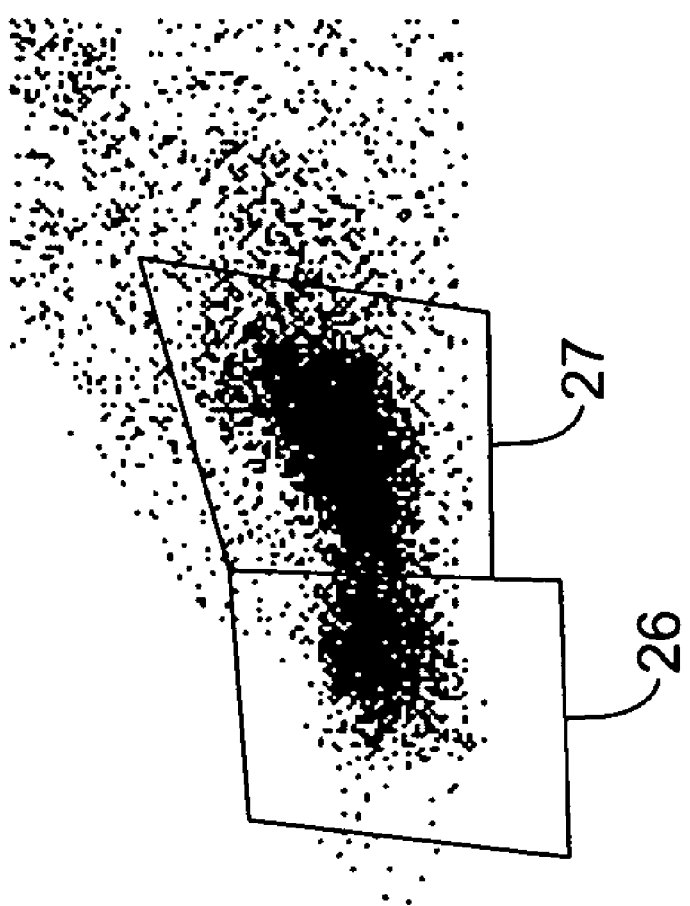
FIG. 4 is an illustrative scattergram of a grouping of two-sized particles.

FIG. 4 is a schematic diagram of a close-up of an illustrative output of a single frame showing a grouping of two sizes of beads. This illustrative example of a frame does not appear to significantly indicate an optimal core stream. The frame of FIG. 4 may appear on the display 18 of the output 16 for the core stream 10. The two groups 26 and 27 of dots 25 show the 6 micrometer and 5 micrometer sized particles 20 and 21, respectively, in the core stream 10. This frame of the groupings and other frames of the same run may be analyzed to determine the stability or other condition of a core stream 10.

In the above-noted runs, the number of particles in the flow channel may be accounted for each frame to aid in determining a sufficient core stream for adequate data acquisition. In actual test situations, the particles 20 and 21 may have other sizes and shapes. The relative position of the dots in a frame of a fairly stable flow may reveal the sizes of the respective particles by several groupings of the dots. Such scattergrams may be used to identify various types of particles according to size and other characteristics.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A method for detecting an optimum core stream in a channel, comprising:
   at a starting time, providing a sample of particles to form a core stream that flows in a channel;
   directing light at the particles of the core stream flowing in the channel;
   detecting light scattered by the particles in the core stream during a series of time intervals;
   converting the light scattered by the particles detected at a forward angle light scattering (FALS) angle and a small angle light scattering (SALS) angle, into FALS versus SALS data for each interval of time of the series of time intervals after the starting time;
   analyzing the FALS versus SALS data for each interval of time; and
   selecting a time duration from the series of time intervals where the FALS versus SALS data exhibit an approximately certain count and grouping of data.

2. The method of claim 1, wherein the certain count and grouping of data indicate a core stream sufficient for data acquisition.

3. The method of claim 2, wherein the optimum core stream is a core stream sufficient for adequate data accession.

4. The method of claim 3, wherein the particles have approximately the same size.

5. The method of claim 3, wherein the particles have at least two different sizes.

6. The method of claim 5, wherein the core stream is stabilized at the time interval the where FALS versus SALS data reveal at least two significantly tight groupings and an approximately certain count.

7. The method of claim 6, wherein a stabilized core stream is sufficient for adequate data accession.

8. The method of claim 1, wherein the certain grouping of data reveals a core stream sufficient for data taking by a flow device.

9. The method of claim 8, wherein:
   the channel is of a flow device; and
   the selected time duration is a characteristic of the flow device.

10. The method of claim 9, wherein the flow device is a cytometer.

11. The method of claim 9, wherein the flow device is for hematology applications.

12. The method of claim 9, wherein the flow device is for environmental applications.

13. The method of claim 9, wherein the flow device is for biological warfare applications.

14. The method of claim 9, further comprising detecting a core stream, sufficient for data taking, in a channel of another flow device.

15. An optimization detection system comprising:
   a processor connected to a FALS and SALS detector mechanism situated proximate to a light source arrangement having a flow channel situated between the FALS and SALS detector mechanism and the light source arrangement; and
   wherein:
   the processor is for recording signals from the FALS and SALS detector mechanism;
   the processor is further for providing an output comprising a FALS signal versus a SALS signal for each particle detected in the flow channel;
   the output comprises a plurality of frames;
   each frame of the plurality of frames contains a plot of the FALS signal versus the SALS signal for each particle detected in the flow channel for a time interval; and
   the time interval is of a series of time intervals beginning at an entry of particles into the flow channel to form a core stream.

16. The system of claim 15, wherein the frames of plots of the FALS signals versus the SALS signals are reviewable for determination of a condition of a core stream of particles in the flow channel during each time interval.

17. The system of claim 16, wherein:
   the condition of the core stream determines whether adequate data may be taken from the core stream;
   if the condition of the core stream indicates that adequate data may be taken form the core stream, then a time interval of that condition is identified;
   a duration of time is identified between the time interval and the entry of particles into the flow channel; and
   the duration of time indicates when adequate data accession of the particles may be performed.

18. The system of claim 15, wherein the processor comprises an algorithm for processing the signals from the FALS and SALS detector mechanism to detect when a core stream is adequate for data taking.

19. A method for detecting an optimum core stream in a flow channel, comprising:
   beginning an insertion of particles to form a core stream sheathed by a fluid to flow in a channel;
   directing light at the particles in the channel;
   detecting and converting light scattered by the particles into electrical signals;
   processing the electrical signals in accordance with an algorithm for a determination of when the core stream is optimum for data taking;
   measuring the lapsed time between the insertion of particles to form the core stream and when the core steam is optimum for data taking; and
   plotting the electrical signals as FALS versus SALS data in a frame during a time interval; and
   wherein:
   the detecting light scattered by the particles is of light at a forward angle light scattering (FALS) angle and a small angle light scattering (SALS) angle;
   a series of time intervals occur during the lapsed time after the insertion of particles; and
   the frames of the time intervals are evaluated and an at least one frame is selected indicating that the core stream is optimum for data taking.

20. The method of claim 19, wherein:
   the at least one frame selected is of an identifiable time interval of the series of time intervals;
   the time intervals have equal durations; and
   a duration of time after the insertion of particles is determined according to a number of time intervals since the insertion of particles to the identifiable time interval.

21. The method of claim 20, the duration of time is the amount of time after the insertion of particles that the core stream is sufficiently stable for data taking from the channel.

22. The method of claim 21, wherein:
   the channel is of a flow device; and
   the duration of time is a characteristic of the flow device.

23. The method of claim 22, further comprising detecting an optimum core stream in a channel of another flow device in accordance with claims 19 through 22.

24. The method of claim 22, wherein the flow device is a cytometer.

25. The method of claim 22, wherein the flow device is for hematology applications.

26. The method of claim 22, wherein the flow device is for biological warfare applications.

27. The method of claim 22, wherein the flow device is for environmental applications.

28. The method of claim 20, wherein the particles are beads of similar sizes.

29. The method of claim 20, wherein the particles are beads of several different sizes.

30. Means for detecting an optimum core stream in a channel of a flow device, comprising:
   means for providing particles to form a core stream that flows in a channel starting at time zero;
   means for directing light at the particles of the core stream flowing in the channel; and
   means for determining an optimum core stream from light scattered by the particles; and
   wherein the means for determining an optimum core stream comprises:
      means for detecting light scattered by the particles at a set of scattering angles;
      means for converting detected light into data signals;
      means for analyzing the data signals for each time interval after time zero; and
      means for selecting a time interval where the data signals indicate an optimum core stream sufficient for data accession.

31. The means of claim 30, wherein the particles are about the same size.

32. The means of claim 30, wherein the flow device is a cytometer.

33. The means of claim 30, wherein the flow device is for hematology applications.

34. The means of claim 30, wherein the flow device is a for biological warfare applications.

35. The means of claim 30, wherein the flow device is for environmental applications.

36. A method for detecting an optimum core stream in a channel, comprising:
   providing a sample of particles to form a core stream that flows in a channel;
   directing light at the particles of the core stream flowing in the channel;
   detecting light scattered by the particles in the core stream during a series of time intervals;
   converting the light, scattered by the particles detected at a first light scattering angle and a second light scattering angle, into first light scattering angle versus second light scattering angle data for a series of time intervals;
   analyzing the first light scattering angle versus second light scattering angle data for the series of time intervals; and
   selecting a time duration from the series of time intervals where the first light scattering angle versus second light scattering angle data exhibit an approximately certain count and grouping of data.

37. The method of claim 36, wherein the certain count and grouping of data indicate a core stream sufficient for data acquisition.

38. The method of claim 37, wherein the optimum core stream is a core stream sufficient for adequate data accession.

39. The method of claim 38, wherein the particles have at least two different sizes.

40. The method of claim 39, wherein the core stream is stabilized at the time interval the where the first light scattering angle versus second light scattering angle data reveal at least two significantly tight groupings and an approximately certain count.

41. The method of claim 36, wherein the certain grouping of data reveals a core stream sufficient for data taking by a flow device.

42. The method of claim 41, wherein:
   the channel is of a flow device; and
   the selected time duration is a characteristic of the flow device.

* * * * *